(12) United States Patent
Bartels et al.

(10) Patent No.: US 11,819,655 B2
(45) Date of Patent: Nov. 21, 2023

(54) VALVE, IN PARTICULAR FOR A DEVICE FOR ADMINISTERING A LIQUID MEDICAMENT, AND A CORRESPONDING DEVICE FOR ADMINISTERING A LIQUID MEDICAMENT

(71) Applicant: SOFTHALE NV, Diepenbeek (BE)

(72) Inventors: Frank Bartels, Hattingen (DE); Jürgen Rawert, Cologne (DE)

(73) Assignee: SOFTHALE NV, Diepenbeek (BE)

( * ) Notice: Subject to any disclaimer, the term of this patent is extended or adjusted under 35 U.S.C. 154(b) by 0 days.

(21) Appl. No.: 17/643,310

(22) Filed: Dec. 8, 2021

(65) Prior Publication Data

US 2022/0203082 A1    Jun. 30, 2022

Related U.S. Application Data

(63) Continuation of application No. 16/333,791, filed as application No. PCT/EP2017/073147 on Sep. 14, 2017, now Pat. No. 11,224,734.

(30) Foreign Application Priority Data

Sep. 15, 2016   (DE) .......................... 102016117396.7

(51) Int. Cl.
*A61M 39/24* (2006.01)
*F04B 19/00* (2006.01)
(Continued)

(52) U.S. Cl.
CPC ........ *A61M 39/24* (2013.01); *A61M 5/16881* (2013.01); *A61M 16/208* (2013.01);
(Continued)

(58) Field of Classification Search
CPC .......... A61M 2039/2493; A61M 39/24; A61M 5/16881; A61M 16/208; A61M 11/00;
(Continued)

(56) References Cited

U.S. PATENT DOCUMENTS 6,290,685 B1    9/2001 Insley et al.
6,977,042 B2   12/2005 Kadel et al.
(Continued)

FOREIGN PATENT DOCUMENTS

EP    0 153 110       8/1985
EP    1493492 A1      1/2005
(Continued)

OTHER PUBLICATIONS

International Search Report for International Application No. PCT/EP2017/073147, dated Dec. 14, 2017, 3 pages.

*Primary Examiner* — Katherine H Schwiker
*Assistant Examiner* — Rachel T. Smith
(74) *Attorney, Agent, or Firm* — Hoxie & Associates LLC

(57) ABSTRACT

The invention relates to a valve, in particular for a device for administering a liquid medicament, with a valve body (1) which has an interior (2) for receiving a liquid (20), wherein the valve body (1) has a liquid inlet (3) and an opposite liquid outlet (4) which both open into the interior (2), wherein the interior (2) accommodates a large number of micro channels (5) which extend in connection direction (x) between the liquid inlet (3) and the liquid outlet (4). A corresponding device for administering a liquid medicament is also described.

23 Claims, 4 Drawing Sheets

(51) Int. Cl.
- *A61M 16/20* (2006.01)
- *F04B 23/02* (2006.01)
- *F04B 13/00* (2006.01)
- *F04B 53/10* (2006.01)
- *F16K 99/00* (2006.01)
- *A61M 5/168* (2006.01)
- *B01L 3/00* (2006.01)
- *A61M 11/00* (2006.01)

(52) U.S. Cl.
CPC ............ *F04B 13/00* (2013.01); *F04B 19/006* (2013.01); *F04B 23/02* (2013.01); *F04B 53/10* (2013.01); *F16K 99/0021* (2013.01); *F16K 99/0057* (2013.01); *A61M 11/00* (2013.01); *A61M 2039/2493* (2013.01); *A61M 2202/04* (2013.01); *B01L 3/502738* (2013.01)

(58) Field of Classification Search
CPC .......... A61M 2202/04; A61M 5/14248; A61M 5/142; A61M 5/1413; A61M 5/145; A61M 2005/14268; A61M 5/1456; A61M 5/158; A61M 2005/14573; A61M 2205/12; A61M 2205/122; A61M 5/14228; A61M 5/14232; F04B 13/00; F04B 23/02; F04B 53/10; F16K 99/0021; F16K 99/0057; B01L 3/502738
See application file for complete search history.

(56) References Cited

U.S. PATENT DOCUMENTS

| | | | |
|---|---|---|---|
| 9,174,211 | B2 | 11/2015 | Jones et al. |
| 11,224,734 | B2* | 1/2022 | Bartels .................. A61M 39/24 |
| 2004/0159319 | A1 | 8/2004 | Kadel et al. |
| 2005/0171480 | A1* | 8/2005 | Mukerjee ............ A61B 5/14514 |
| | | | 604/173 |
| 2007/0160474 | A1* | 7/2007 | Iida ..................... F16K 99/0057 |
| | | | 416/27 |
| 2012/0138049 | A1* | 6/2012 | Wachtel ............ A61M 16/0816 |
| | | | 128/200.14 |

FOREIGN PATENT DOCUMENTS

| | | | |
|---|---|---|---|
| EP | 2 896 457 | 7/2015 | |
| EP | 2896457 A1 * | 7/2015 | .......... B01L 3/50273 |
| WO | WO 1997/024528 | 7/1997 | |
| WO | WO 2005/000476 | 1/2005 | |
| WO | WO 2012/007315 | 1/2012 | |
| WO | WO 2012/098140 | 7/2012 | |
| WO | WO 2013/029159 | 3/2013 | |
| WO | WO 2013/090459 A1 | 6/2013 | |

* cited by examiner

A: Reservoir
B: One-Way Valve
C: Pump with Pump Chamber
D: Valve of the Present Disclosure
E: Medicine Outlet
F: Device

VALVE, IN PARTICULAR FOR A DEVICE FOR ADMINISTERING A LIQUID MEDICAMENT, AND A CORRESPONDING DEVICE FOR ADMINISTERING A LIQUID MEDICAMENT

CROSS-REFERENCE TO RELATED APPLICATIONS

This application is a continuation of U.S. application Ser. No. 16/333,791, filed on Mar. 15, 2019, which is a National Stage Entry under 35 U.S.C. § 371 claiming priority to and the benefit of PCT Application No. PCT/EP2017/073147, filed Sep. 14, 2017, which claims priority to and the benefit of German Application No. 10 2016 117 396.7, filed on Sep. 15, 2016, the contents of each of which are hereby incorporated by reference in their entireties.

BACKGROUND OF THE INVENTION

The invention relates to a valve, in particular for a device for administering a liquid medicine, and a corresponding device for administering a liquid medicine.

DESCRIPTION

Devices for administering a liquid medicine are known from the prior art, said devices having a reservoir that is connected to a pump system. The outlet side of the pump is connected to a medicine outlet, for example to a tube or pipe, or to an atomiser. Often, the pump chamber of the pump has an inlet and an outlet valve. The inlet valve seals the pump chamber exactly when the pump generates an output pressure to provide the medicine via the tube, pipe or the vaporiser, in order to avoid the medicine flowing back into the reservoir. A negative pressure is generated in the pump chamber to refill the pump chamber, whereby the medicine flows from the reservoir, through the opening inlet valve into the pump chamber, while the outlet valve closes, in order to avoid the medicine flowing back out of the tube, pipe or vaporiser. The valves are thus formed as established one-way valves, for example as non-return valves. WO 2013/191011 A1, U.S. Pat. No. 8,628,517 B2 and WO 201.3/072790 A1 describe similar devices.

In particular with medical applications, it is often desirable that the device for administering the liquid medicine is constructed to be as small as possible and thus takes up less space. In particular, however, the inlet and outlet valves that are known from the prior art and are usually purely mechanical cannot be non-limitedly reduced in size, such that there is the need to improve such valves further still, or even make them completely superfluous, where necessary.

It is thus the object of the invention to propose a generic valve and a corresponding device for administering a liquid medicine, which have dimensions that are as small as possible.

According to the invention, this object is solved by a valve having the features of claim 1. Subordinate claim 12 relates to a corresponding device for administering a liquid medicine. The dependent claims 2 to 9 each relate to advantageous embodiments of the invention.

The valve according to the invention has a valve body, which comprises an inner space for receiving a liquid, in particular a liquid medicine. The valve body has a liquid inlet and an opposite liquid outlet, which both open out into the inner space. A plurality of microchannels is arranged in the inner space, which extend in the connection direction between the liquid inlet and the liquid outlet.

The valve according to the invention makes use of the capillary effect. It is known that, because of capillary forces, liquids wet surfaces and can move through complex structures. Here, the energy required for the liquid movement is by the difference of the atomic attractive forces between the liquid atoms inside of the liquid and the atomic attractive forces between the liquid atoms that are on the liquid surface and thus at the boundary surface between the liquid and a gas. The boundary surface between a liquid and a gas is also called the free surface. Energy also has to be expended for the removal of liquid atoms from the free surface, such that atoms previously lying deeper and found inside of the liquid form the free surface. Thus, a force must be expended in order to remove liquid portions of strongly wetting surfaces.

In one embodiment of the invention, the valve body forms a liquid channel, which is bordered by side walls. The side walls can be parallel side walls of a channel that is polygonal or round in cross-section, for example circular.

In one embodiment, the inner space has a cross-sectional area which is greater than the cross-sectional area of the microchannels, wherein a cross-sectional area ratio between the microchannels and the inner space is preferably between 1:5 and 1:1000 and particularly preferably between 1:50 and 1:100. The microchannels preferably have a diameter between 1 µm and 200 µm and particular preferably between 5 µm and 20 µm.

In one embodiment of the invention, the microchannels are formed by a grid made of parallel, rod-shaped boundary elements, or from several parallel layers of a grid that are arranged offset in relation to one another, said grid being formed from parallel rod-shaped boundary elements. Here, the boundary elements can extend perpendicularly to the connection direction between the liquid inlet and the liquid outlet. The boundary elements preferably have a round, in particular circular, or a polygonal cross-section. For example, the boundary elements can have a diameter between 0.5 µm and 50 µm, preferably between 3 µm and 15 µm. Here, the length of the boundary elements can be a few µm up to the full diameter of the inner space of the valve body; particularly preferably, the length of the boundary elements is between 20% and 80% of the inner space diameter perpendicular to the connection direction between the liquid inlet and the liquid outlet. In addition, the boundary elements can extend starting from an inner side of the side wall bordering the inner space of the valve body in the direction of an opposite side wall, without reaching this, such that a spacing between the boundary elements and the respectively opposite side wall is formed. This embodiment is also characterised, in particular, in that it is simple in terms of production.

To increase the adhesion between the boundary elements and a liquid, it is provided in one embodiment of the invention that the surface of the boundary elements has a functional coating, for example a hydrophilic coating. In addition, the inner side of the channel can, furthermore, be hydrophobically coated.

In yet another embodiment of the invention, the inner space, the liquid inlet and the liquid outlet have the same cross-sectional geometry perpendicular to the connection direction. As a result, a valve geometry that is particularly compact and can be simply produced is obtained.

Here, it can be provided that the valve body has parallel side walls whose inner sides border the inner space, wherein the side walls open out into the liquid inlet or the liquid outlet on opposite ends. A valve that can be simply produced is obtained in that, with the embodiment mentioned last, the valve body has a constant cross-section over its entire length between the liquid inlet and the liquid outlet.

The valve body can have a round, in particular circular, or a polygonal cross-section.

According to a different aspect, the invention relates to a device for administering a liquid medicine, having a reservoir in which a medicine is held or can be held, and having a pump, which has a pump chamber, which is fluidically connected to the reservoir via a one-way valve that is only transmissive in the direction from the reservoir into the pump chamber, and which is fluidically connected to a medicine outlet via a valve according to one of the preceding claims.

BRIEF DESCRIPTION OF THE FIGURES

Further details of the invention are explained by means of the figures below. Here are shown.

Figure 1:
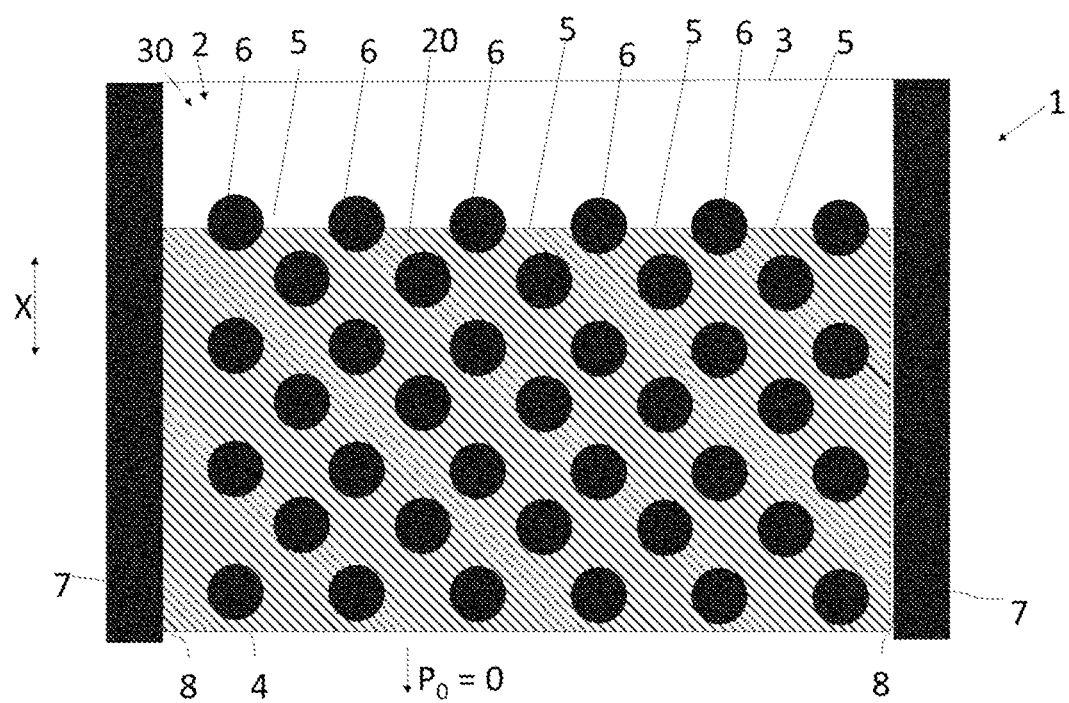
FIG. 1 a schematic longitudinal cross-section through an embodiment of the valve according to the invention without negative pressure applied.

With the valve depicted in FIG. 1, the valve body 1 is depicted in longitudinal cross-section. The valve body 1 is bordered by opposite parallel side walls 7. The side walls 7 border an inner space 2 with their inner sides 8, in which inner space 2 a liquid 20, for example a medicine, is received. On opposite sides of the valve body 1, a liquid inlet 3 or a liquid outlet 4 is formed. The liquid inlet 3 and the opposite liquid outlet 4 have exactly the same cross-section as the remaining valve body 1, in particular as the inner space 2. A pump having a pump chamber of a device can be attached, for example, to the liquid outlet 4 for administering a liquid medicine.

The valve body 1 can, for example, have a circular cross-section, or a polygonal, for example a rectangular or, in particular, a quadratic one. The boundary elements 6 shown in cross-section in FIG. 1 are rod-shaped grid bars that extend in parallel to one another and perpendicularly to the drawing plane. In each case, two adjacent boundary elements 6 form a microchannel 5 between them, which extends in the connection direction x between the liquid inlet 3 and the liquid outlet 4 and is open to the two inlets 3, 4.

As depicted in FIG. 1, the microchannels are formed from several parallel layers of a grid that are arranged offset in relation to one another, said grid being formed from parallel, rod-shaped boundary elements.

When there is no negative pressure (Po=0) applied to the liquid outlet 4, the liquid 20 forms a substantially planar, free surface, as is shown in FIG. 1, between itself and the gas 30.

Only when a negative pressure (P1>0) is applied to the liquid outlet 4 (see FIG. 2) does the free surface form a concave geometry between the liquid 20 and the gas 30. With growing negative pressure, the radius of the concave boundary surface decreases between the liquid 20 and the gas 30. In FIG. 3, the case in which P2>P1 applies is shown.

The radius of curvature of the free surface is dependent on the so-called Laplace pressure. This pressure increases with a boundary radius that is getting smaller. Thus, when the negative pressure exceeds the maximum Laplace pressure that is valid for the microchannel structure depicted in FIGS. 1 to 3, the liquid is transported out of the valve body 1. The valve according to the invention is thus suitable, in particular, for the use as an outlet valve with a generic device for administering a liquid medicine.

In principle, the Laplace pressure increases proportionally to the surface tension of the liquid. In order to thus adjust the threshold value for the negative pressure in which the liquid is transported out of the valve body 1, with the surface tension given, to a certain value, it can be necessary to correspondingly align the diameter of the microchannels 5, and, with that, the spacing of the boundary elements 6 in relation to one another.

Figure 2:
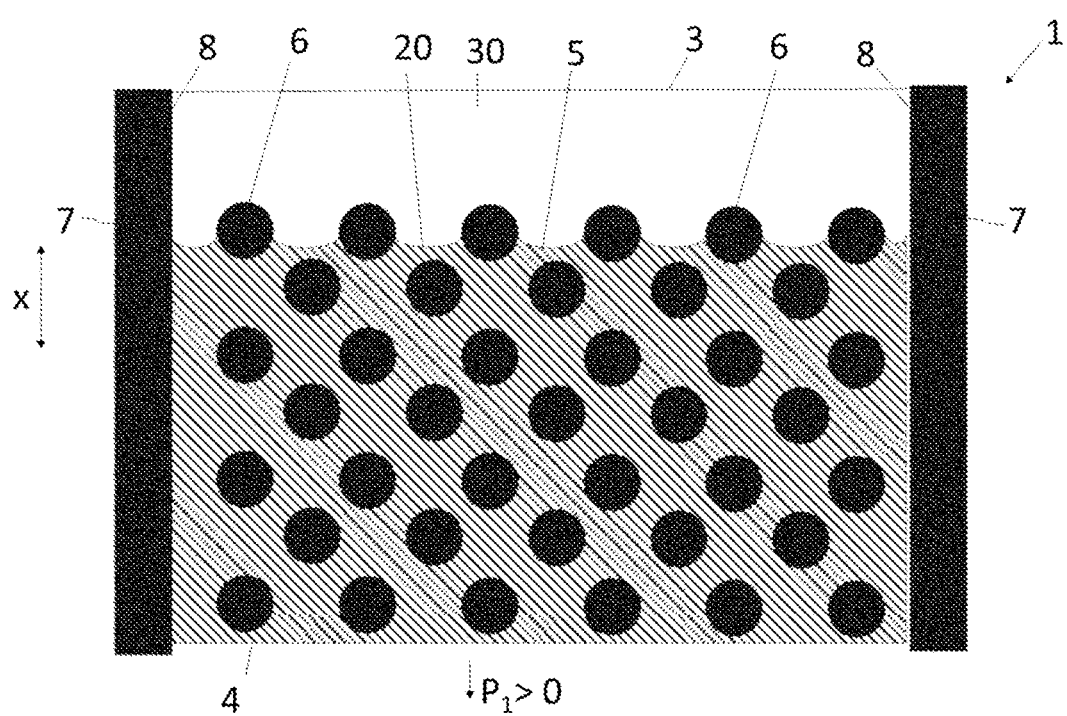
FIG. 2 a schematic longitudinal cross-section of the valve according to FIG. 1 having a negative pressure P1>0 applied.
Figure 3:
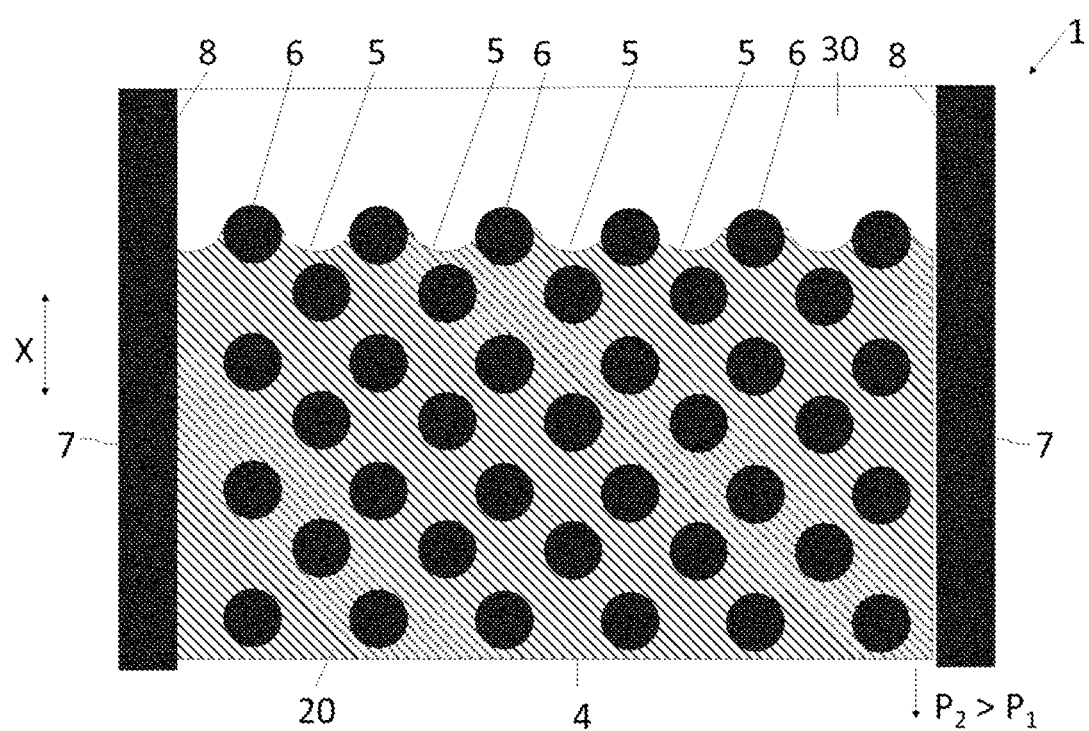
FIG. 3 a schematic longitudinal cross-section of the valve according to FIGS. 1 and 2 with a negative pressure P2>P1 applied.
Figure 4:
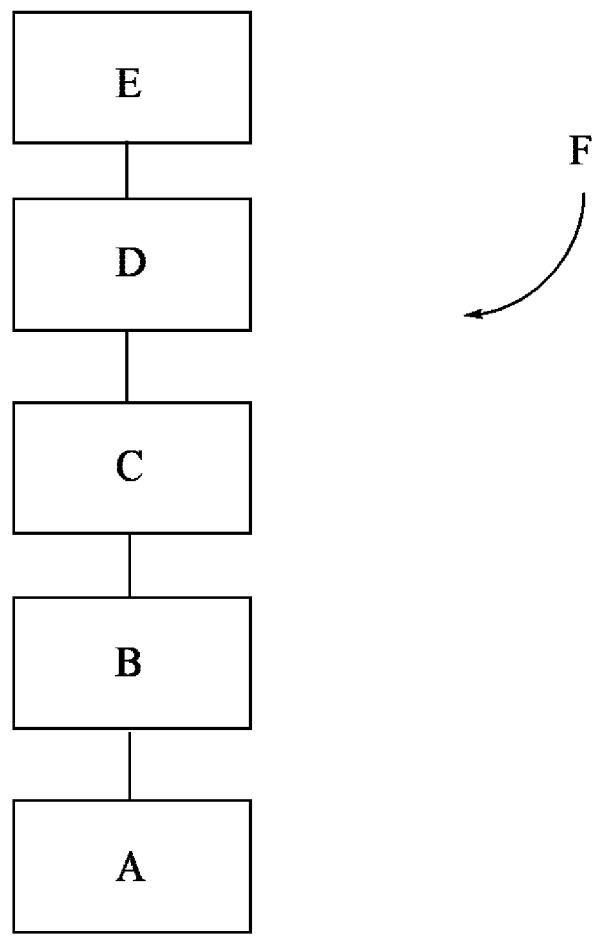
FIG. 4 A schematic representation of a Device for administering a liquid medicine in accordance with the present disclosure.

The embodiment shown in FIGS. 1 to 3 can, for example, have an inner space diameter perpendicular to the inner sides 8 of the side walls between roughly 1 µm and 500 µm. Preferably, this diameter is between 10 µm and 100 µm.

The diameter of the microchannels 5, and, with that, the free spacing or the clearance between the boundary elements 6 can lie between 0.5 and 50 µm. Preferably, the free spacing or the clearance between the boundary elements 6 is between 3 and 15 µm.

The valve according to the invention has the advantage in that the required structures can be produced by means of established micro-structuring methods, for example by means of micro-injection moulding or silicon etching methods.

The features of the invention disclosed in the description above, in the drawing and in the claims, can be essential for the realisation of the invention both individually and in any combination.

LIST OF REFERENCE NUMERALS

1 Valve body
2 Inner space
3 Liquid inlet
4 Liquid outlet
5 Microchannel
6 Boundary element
7 Side wall
8 Inner side
x Connection direction between the liquid inlet and the liquid outlet

The invention claimed is:

1. A valve for a device for administering a liquid medicine, having a valve body which has an inner space for receiving a liquid, wherein the valve body has a liquid inlet and an opposite liquid outlet, which both open out into the inner space, wherein a plurality of microchannels is arranged in the inner space, said plurality of microchannels extending in a connection direction between the liquid inlet and the liquid outlet, wherein the plurality of microchannels are formed by a grid made of parallel, rod-shaped boundary elements, or of several parallel layers of said grid that are arranged offset in relation to one another,
  wherein the entirety of said parallel, rod-shaped boundary elements in the valve body are arranged in the inner space; and
  wherein the inner space, the liquid inlet and the liquid outlet have the same cross-sectional area perpendicular to the connection direction.

2. The valve according to claim 1, in which each of the plurality of microchannels have a diameter between 1 μm and 200 μm.

3. The valve according to claim 2, in which each of the plurality of microchannels have a diameter between 5 μm and 20 μm.

4. The valve according to claim 1, in which the boundary elements extend perpendicularly to the connection direction between the liquid inlet and the liquid outlet.

5. The valve according to claim 1, in which a length of the boundary elements is between 20% and 80% of a diameter of the inner space perpendicular to the connection direction between the liquid inlet and the liquid outlet, wherein the boundary elements extend starting from an inner side of a side wall bordering the inner space of the valve body toward an opposite side wall, without reaching this, such that a spacing between the boundary elements and the opposite side wall is formed.

6. The valve according to claim 1, in which the boundary elements have a round or a polygonal cross-section.

7. The valve according to claim 6, wherein the boundary elements have a circular cross-section.

8. The valve according to claim 1, in which the inner space, the liquid inlet and the liquid outlet have the same cross-sectional area perpendicular to the connection direction.

9. The valve according to claim 8, in which the valve body has a constant cross-section across its entire length between the liquid inlet and the liquid outlet.

10. The valve according to claim 1 in which the valve body has parallel side walls, whose inner sides border the inner space, wherein the side walls open out into the liquid inlet or the liquid outlet on opposite ends.

11. The valve according to claim 1, in which the valve body has a round or a polygonal cross-section.

12. The valve according to claim 11, in which the valve body has a circular cross-section.

13. The valve according to claim 1, in which, to increase the adhesion between the boundary elements and a liquid, a surface of the boundary elements has a functional coating.

14. The valve according to claim 13, wherein the functional coating is a hydrophilic coating.

15. The valve according to claim 1, wherein the cross-sectional area ratio between the microchannels and the inner space is between 1:5 and 1:1000.

16. The valve according to claim 1, wherein the cross-sectional area ratio between the microchannels and the inner space is between 1:50 and 1:100.

17. The valve according to claim 1, wherein the boundary elements have a diameter between 0.5 μm and 50 μm.

18. The valve according to claim 1, wherein the boundary elements have a diameter between 3 μm and 15 μm.

19. The valve according to claim 1, wherein the valve is produced by means of micro-injection moulding.

20. The valve according to claim 1, wherein the valve is produced by means of silicon etching methods.

21. The valve according to claim 1, wherein in the absence of an applied pressure, the liquid is held stationary within the valve body, and when the applied pressure exceeds a threshold amount, the liquid is transported out of the valve body.

22. The valve according to claim 1, wherein the threshold amount is the maximum Laplace pressure for the valve body.

23. A device for administering a liquid medicine, having a reservoir, in which a medicine is held or can be held, and having a pump, which has a pump chamber, which is fluidically connected to the reservoir via a one-way valve that is only transmissive in a direction from the reservoir into the pump chamber, and that is fluidically connected to a medicine outlet via a valve according to claim 1.

* * * * *